United States Patent [19]

Gaiser et al.

[11] Patent Number: 5,002,532
[45] Date of Patent: * Mar. 26, 1991

[54] TANDEM BALLOON DILATATION CATHETER

[75] Inventors: John W. Gaiser, Mountain View; Wilfred J. Samson, Saratoga, both of Calif.

[73] Assignee: Advanced Cardiovascular Systems, Inc., Santa Clara, Calif.

[*] Notice: The portion of the term of this patent subsequent to Jun. 28, 2005 has been disclaimed.

[21] Appl. No.: 370,085

[22] Filed: Jun. 21, 1989

Related U.S. Application Data

[63] Continuation of Ser. No. 169,111, Mar. 9, 1988, which is a continuation of Ser. No. 696, Jan. 6, 1987, abandoned.

[51] Int. Cl.$^5$ ............................................. A61M 25/10
[52] U.S. Cl. ..................................... 604/101; 606/194
[58] Field of Search .................. 128/344, 348.1, 356; 604/96-103, 86, 283; 606/191, 192, 194

[56] References Cited

U.S. PATENT DOCUMENTS

| | | | |
|---|---|---|---|
| 1,014,228 | 1/1911 | Kellogg | 604/99 |
| 3,426,744 | 2/1969 | Ball | 604/96 |
| 3,467,101 | 9/1969 | Fogarty et al. | 128/348.1 |
| 4,323,071 | 4/1982 | Simpson et al. | 128/343 |
| 4,403,612 | 9/1983 | Fogarty | 128/344 |
| 4,445,892 | 5/1984 | Hussein et al. | 604/101 |
| 4,582,181 | 4/1986 | Samson | 128/348.1 |
| 4,630,609 | 12/1986 | Chin | 128/344 |
| 4,655,746 | 4/5198 | Daniels et al. | 604/53 |
| 4,753,238 | 6/1988 | Gaiser | 128/344 |

FOREIGN PATENT DOCUMENTS

| | | | |
|---|---|---|---|
| 0654214 | 2/1986 | Switzerland | 604/101 |
| 8606285 | 11/1986 | World Int. Prop. O. | 128/344 |

Primary Examiner—C. Fred Rosenbaum
Assistant Examiner—William W. Lewis
Attorney, Agent, or Firm—Fulwider, Patton, Lee & Utecht

[57] ABSTRACT

Tandem balloon dilatation catheter assembly having a flexible elongate member with proximal and distal ends. The flexible elongate member is provided with at least first and second lumens extending therethrough. First and second balloons are carried by the distal extremity of the flexible elongate member and are spaced apart longitudinally thereof. The first balloon has a diameter which is less than the diameter of the second balloon. The first balloon is disposed distally of the second balloon. Communication is established between the interior of the first balloon and the first lumen and between the interior of the second balloon and the second lumen.

1 Claim, 2 Drawing Sheets

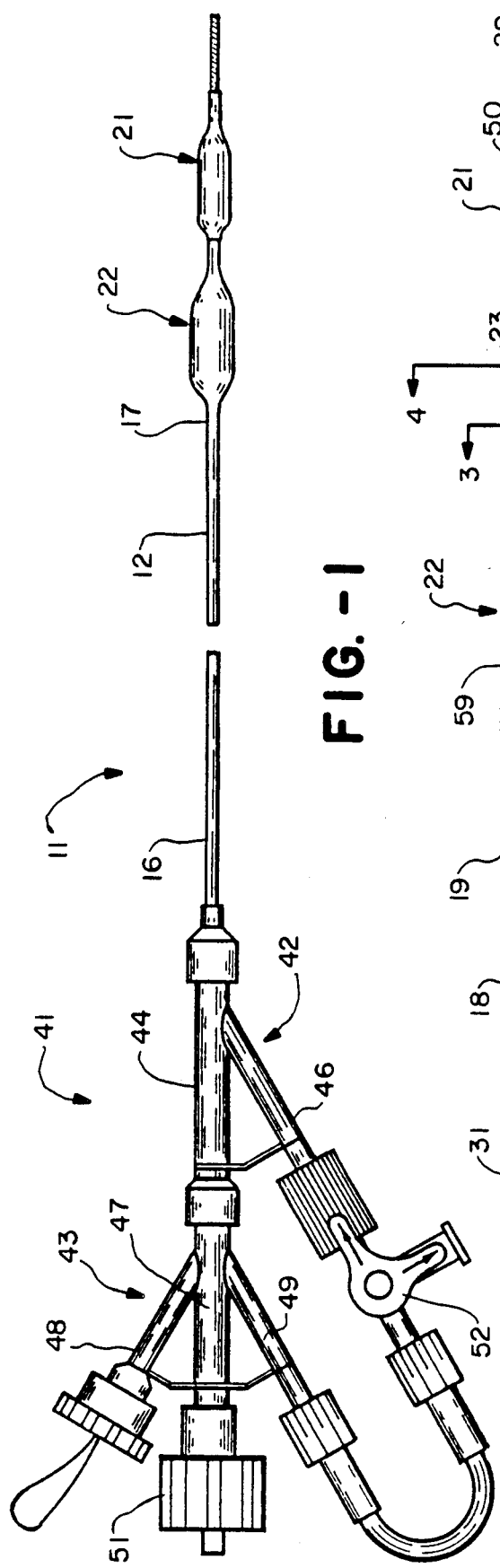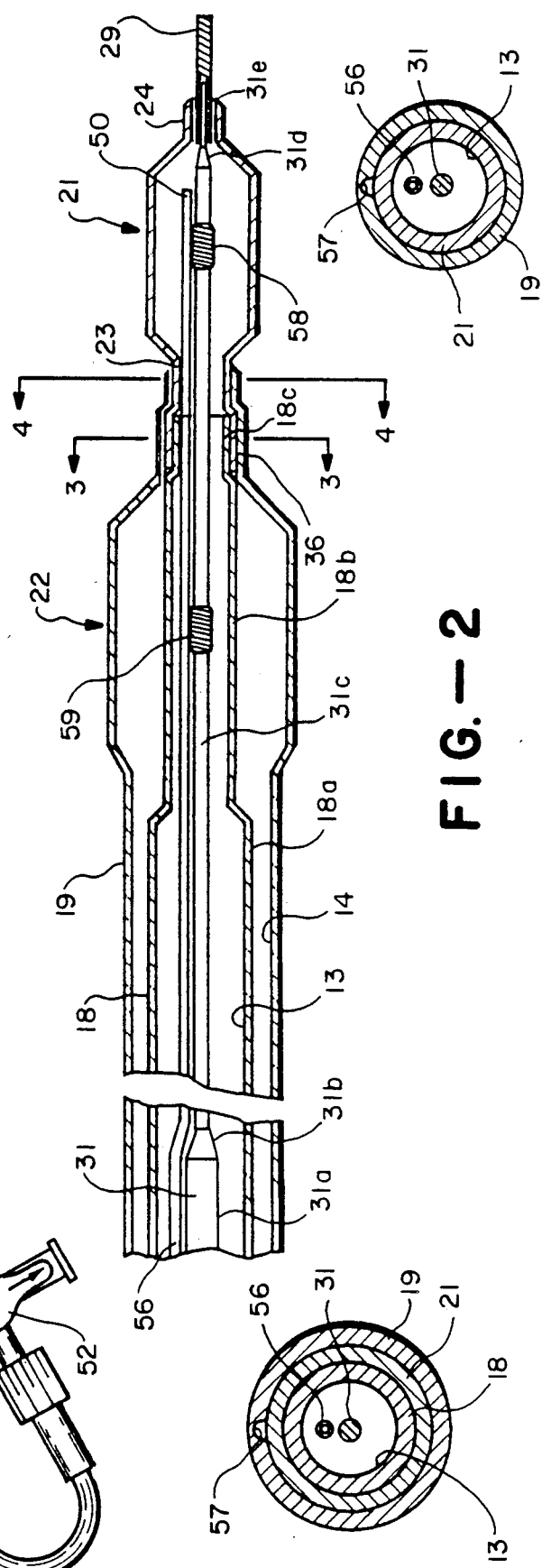

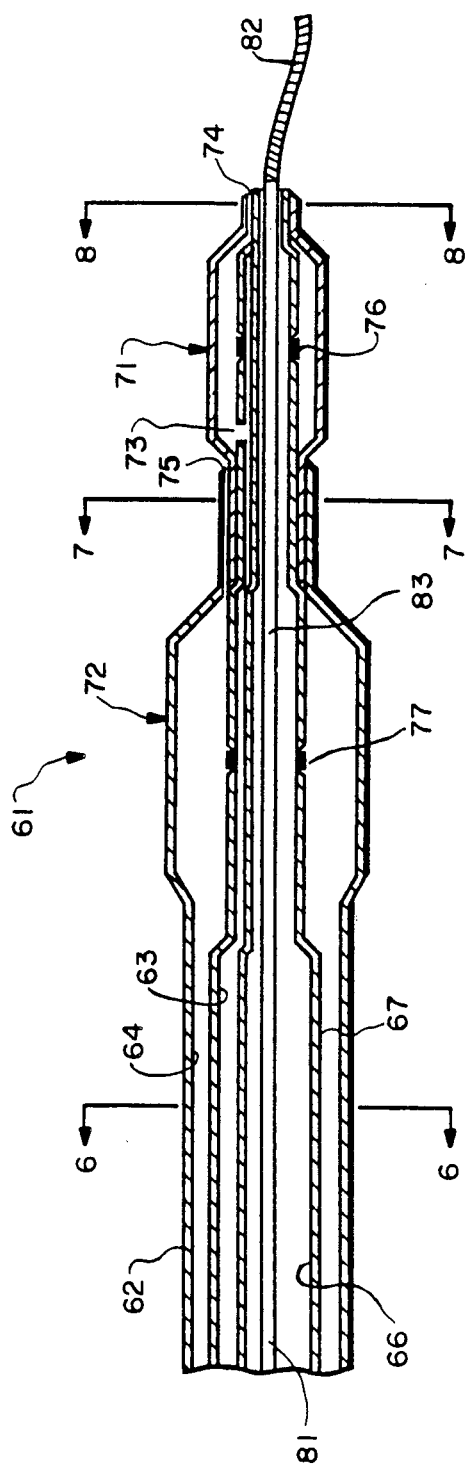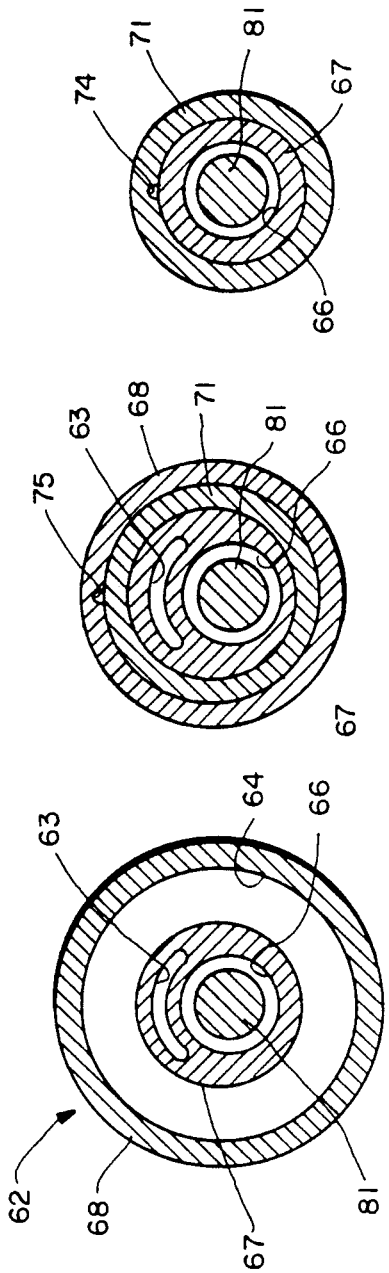

TANDEM BALLOON DILATATION CATHETER

This is a continuation of application Ser. No. 169,111, filed Mar. 9, 1988, which is a continuation of Ser. No. 000,696 filed Jan. 6, 1987, now abandoned.

This invention relates to balloon dilatation catheters and more particularly to tandem balloon dilatation catheters.

Balloon dilatation catheters have heretofore been provided In the past when it has been necessary to utilize two different size balloons in connection with opening a stenosis in a vessel, it has been necessary to first insert the dilatation catheter with a smaller balloon and thereafter withdraw this dilatation catheter from the vessel and then insert a dilatation catheter having a balloon of larger diameter. Such a procedure in the past has been time consuming. There is therefore a need for a new and improved balloon dilatation catheter.

In general, it is an object of the present invention to provide a balloon dilatation catheter and method which utilizes tandem balloons to eliminate the need for catheter exchanges.

Another object of the invention is to provide a catheter and method of the above character in which the tandem balloons are of different sizes.

Another object of the invention is to provide a catheter and method of the above character which utilizes a multi-port adapter to permit independent rapid inflation and deflation of the tandem balloons.

Another object of the invention is to provide a dilatation catheter and method of the above character which is adapted to be used with movable and stationary guidewires.

Another object of the invention is to provide a dilatation catheter and method of the above character in which the balloons can be readily vented.

Additional objects and features of the invention will appear from the following description in which the preferred embodiments are set forth in detail in conjunction with the accompanying drawings.

FIG. 1 is a side elevational view of a balloon dilatation catheter having tandem balloons incorporating of the present invention.

FIG. 2 is an enlarged cross-sectional view of the distal extremity of the catheter shown in FIG. 1.

FIG. 3 is a cross-sectional view taken along the line 3—3 of FIG. 2.

FIG. 4 is a cross sectional view taken along the line 4—4 of FIG. 2.

FIG. 5 is a cross-sectional view of a balloon dilatation catheter incorporating the present invention similar to FIG. 2, but showing the use of a movable guide wire.

FIG. 6 is a cross-sectional view taken along the line 6—6 of FIG. 5.

FIG. 7 is a cross-sectional view taken along the line 7—7 of FIG. 5.

FIG. 8 is a cross-sectional view taken along the line 8—8 of FIG. 5.

In general, the tandem balloon dilatation catheter assembly of the present invention is comprised of an elongate member having first and second flow passages therein and having proximal and distal ends. First and second balloons are carried by the distal extremity of the flexible elongate member. The first balloon has a diameter substantially less than the diameter of the second balloon. A first balloon is disposed distally of the second balloon. Means is provided for establishing communication between the first of the flow passages and the interior of the first balloon as well as for establishing communication between the second lumen and the interior of the second balloon. Means is secured to the proximal extremity of the flexible elongate member permitting independent inflation and deflation of the first and second balloons through the first and second passages. Means is provided for venting at least one of the balloons.

More specifically as shown in FIG. 1, the tandem balloon dilatation catheter assembly 11 consists of a flexible elongate tubular member 12 formed of a suitable flexible material such as plastic. Suitable materials are disclosed in U.S. Pat. No. 4,323,071. The flexible elongate member 12 is formed so that it provides at least first and second flow passages 13 and 14 extending longitudinally thereof (see FIG. 2). The flexible elongate member 12 has proximal and distal extremities 16 and 17. The flow passage 13 and 14 can be formed in a suitable manner such as by providing a co-axial construction for the tubular member 12 such as shown in FIG. 2 and as disclosed in U.S. Pat. No. 4,323,071 in which an inner tubular member 18 is provided which has the flow passage 13 extending therethrough and an outer tubular member 19 is provided with the flow passage 14 being in the form of an annular flow passage extending between the exterior of the inner tubular member 18 and the interior of the outer tubular member 19. It should be appreciated that if desired, the flow passages 13 and 14 can be formed in a single tubular member by providing two flow passages or lumens 13 and 14 in the tubular member by suitable means such as by extrusion.

First and second tandem balloons 21 and 22 are carried by the distal extremity of the flexible elongate member 12. The first balloon 21 is distal of the second balloon 22 and preferably has the smaller size or smaller outside diameter than the diameter of the second balloon 22. The first balloon 21 can be referred to as a distal balloon with the second balloon 22 being referred to as the proximal balloon.

As can be seen from FIG. 2, means is provided for establishing communication between the first flow passage 13 and the interior of the balloon 21 by having the flow passage 13 open directly into the balloon 21. Means is also provided for establishing communication between the second flow passage 14 and the interior of the second balloon 22 by having the flow passage 14 open directly into the balloon 22. The inner tubular member 18 is provided with a continuous diameter extremity to near the distal extremity. The inner tubular member 18 is provided with necked-down portions 18b and 18c on its distal extremity of progressively smaller diameters portion 18b extends through the balloon 22 whereas portion 18c terminates at the junction of balloon 22 and the balloon 21.

The first or distal balloon 21 can be formed of a separate tubular balloon member or it can be formed integral in the distal extremity of the inner tubular member 18. As shown in FIG. 2 it is formed as a separate tubular member or component which has its proximal necked-down extremity 23 secured to the portion 18c of the distal extremity of the inner tubular member 18 by suitable means such as by using heat shrinkable irradiated material for the balloon member or by utilizing an adhesive to form a fluid-tight seal. The necked-down distal extremity 24 of the balloon member 21 can be necked-down onto a spring tip 29 of a core wire 31 or by utilizing an adhesive to form suitable means such as a fluid-tight seal.

The spring tip 29 can be formed in a manner described in U.S. Pat. No. 4,538,622 and is formed of a suitable radiopaque material such as tungsten or platinum or a combination of the two.

The spring tip 29 is secured to the distal extremity of the core wire 31 in a suitable manner such as by soldering or brazing. The core wire 31 can be formed of a suitable material such as stainless steel. Typically, it can have a diameter of 0.014 to 0.018 inches with progressive tapers to smaller diameters along its distal extremity. As shown in FIG. 2, the core wire 31 extends through the inner or first flow passage 13. The core wire 31 can have a portion 31a of a continuous diameter of 0.016 inch from its proximal end for a distance of approximately 150 centimeters followed by a tapered portion 31b approximately 3 centimeters in length. The cylindrical portion 31c follows having a continuous diameter of 0.008 inch followed by a tapered portion 31d three centimeters in length which is followed by a flattened portion 31e having a thickness of 0.002 to 0.003 inch and a length of 0.5 to 2 centimeters. The portion 31c extends through the balloons 21 and 22.

The second or proximal balloon 22 can be formed integral with the outer tubular member 19 or if desired, it also can be formed as a separate tubular member and bonded thereto by suitable means such as an adhesive. If it is formed integral with the tubular member it can be formed of a heat shrinkable irradiated material in which the distal necked-down extremity 36 can be secured to the proximal extremity of the first balloon 21 by suitable means such as by a shrink fit or by the use of an adhesive.

An adapter assembly 41 of the type described in copending application Ser. No. 000,712, filed Jan. 6, 1987 is secured to the proximal extremity of the elongate member 12 and consists of a two-arm adapter 42 and a three-arm adapter 43. The two-arm adapter 42 consists of a central arm 44 and a side arm 46 and the three-arm adapter consists of a central arm 47 and side arms 48 and 49. The core wire or guide wire 31 extends through central arms 44 and 47 and is connected to a rotation limiting device 51 of the type described in application Ser. No. 760,635, filed July 30, 1985. As described in copending application Ser. No. 000,712, filed Jan. 6, 1987 the arms 49 and 46 are in communication with the flow passages 13 and 14 respectively so that radiographic contrast liquid can be introduced into the passage for inflating and deflating the balloons 21 and 22. This can be accomplished by the use of an inflation/deflation device of the type disclosed in U.S. Pat. No. 4,439,185 coupled to a valve fitting 52 connected to the arms 46 and 49.

Suitable means is provided for venting air from the first and second balloons 21 and 22 as they are filled with the radiographic contrast liquid. By way of example, a vent tube 56 of the type described in U.S. Pat. No. 4,323,071 can be utilized and introduced through the side arm 48 and into the first flow passage or lumen 13 until it extends near the distal extremity of the balloon 21. As can be seen, as the balloon is filled with radiopaque liquid, air in the balloon will be forced into the vent tube and vented to the atmosphere through its proximal extremity. Similarly, another vent tube (not shown) can be provided which is inserted into the second lumen or flow passage 14 and extended into the distal extremity of the balloon 22 so that any air collected in that balloon can also be vented to the atmosphere through the proximal extremity of the vent tube. It should be appreciated that alternative venting means can be utilized, such as a self-venting feature described in application Ser. No. 000,712, filed Jan. 6, 1987 in which a small passage 57 is provided (see FIGS. 3 and 4) for venting the proximal balloon 22 to the atmosphere. The above alternative vent design may also be used on the distal balloon 21, replacing the vent tube 56.

One or more markers which are substantially radiopaque, such as markers 58 and 59 can be provided in each of the balloons 21 and 22 so that the general location of the balloons 21 and 22 can be viewed under a fluoroscope. It should be appreciated that even though the markers 58 and 59 have been shown intermediate the ends of each of the balloons, that if desired two markers can be provided in each of the balloons with one near the distal extremity of the balloon and the other near the proximal extremity of the balloon so that the physician utilizing the catheter can readily ascertain the position of the balloons of the catheter with respect to a stenosis.

Operation and use of the tandem balloon catheter assembly shown in FIGS. 1 and 2 may now be briefly described as follows in performing the method of the present invention. In utilizing the dilatation catheter assembly, a guiding catheter (not shown) is first inserted into the vessel by the use of a guide wire (not shown). The guide wire is then removed. The dilatation catheter assembly 11 prior to introduction of the guiding catheter has been prepared for insertion into the guiding catheter. This has been done by inflating the balloons 21 and 22 by inserting a suitable liquid such as a radiopaque contrast medium into the arms 46 and 49 to inflate the balloons 21 and 22 to ensure that all air is removed from the balloons. The balloons are then deflated by removing the radiopaque liquid.

Assuming that the tandem balloon dilatation catheter assembly is of a type shown in FIG. 1 which uses a guidewire which is fixed at its distal extremity, the dilatation catheter is inserted into the vessel by introducing the same into the guiding catheter and advancing the spring tip across the stenosis. The smaller or distal balloon 21 is advanced across the stenosis and inflated by introducing radiopaque contrast liquid into the balloon 21 through the arm 49.

Thereafter to obtain additional enlargement of the opening in the stenosis, the second balloon 22 can then be advanced into the opening formed by the first balloon 21. It is then inflated by introducing radiopaque liquid through the arm 46. After this balloon 22 has been inflated, it is deflated and the catheter assembly can then be removed. Assuming that the angioplasty procedure has been successful, the guiding catheter can thereafter be removed.

Another embodiment of the invention is shown in FIGS. 5–8 in which a tandem balloon dilatation catheter assembly 61 is shown. The assembly 61 consists of an elongate flexible member 62 which is provided with proximal and distal ends. It also has at least first and second flow passages or lumens 63 and 64 which extend longitudinally of the elongate flexible member 62. In addition, in the embodiment of the invention shown in FIG. 5, an additional or third flow passage or lumen 66 is provided in the elongate flexible member 62. The flow passages or lumens 63, 64 and 66 can be provided in any suitable manner. For example, as shown in FIG. 6, a partial co-axial type construction can be utilized in which the elongate flexible member 62 is comprised of an inner tubular member 67 and an outer tubular member 68. The inner tubular member 67 has a flow passage or lumen 63 extending therethrough which serves as a balloon inflation lumen. The lumen 66 may also be utilized for distal radiopaque dye injection. The second flow passage or lumen 64 is formed by the annular space provided between the inner and outer tubular members 67 and 68. The third lumen 66 is provided within the inner tubular member 67 as shown particularly in FIG. 6. The lumen 66 serves as the guide wire lumen and the lumen 63 serves as the inflation/deflation lumen. The inflation/deflation lumen 63 as shown can be substantially moon-shaped in cross section whereas the guide wire lumen 66 is generally circular in cross section. In this manner, it is possible to provide two lumens in the same inner tubular member without substantially increasing the overall cross-sectional diameter of the inner tubular member 67.

It should be appreciated that if desired, all of the three flow passages or lumens 63, 64 and 66 can be formed in a single tubular member by providing two inflation lumens such as the inflation lumen 63 within the same tubular member and by providing a centrally disposed guide wire lumen 66 in the same tubular member. This can be readily accomplished by extruding such an elongate flexible member. The inner and outer tubular member 67 and 68 can be formed of a suitable material such as plastic, as hereinbefore described.

First and second or distal and proximal dilatation balloons 71 and 72 are carried by the distal extremity of the elongate flexible member 62 and are arranged in tandem or in series as disclosed with respect to the first embodiment of the present invention. As hereinbefore described, integral or separate balloons can be provided. Thus as shown in FIG. 5, a separate balloon 71 has been provided in which distal extremity of the balloon is necked down and sealed to the distal extremity of the inner tubular member 67 by suitable means such as an adhesive or a shrink fit. Similarly, the proximal extremity of the first balloon 71 is necked down and also fitted over the inner tubular member 67 and secured thereto by suitable means such as an adhesive to provide a fluid-tight seal.

Means is provided for establishing communication between the balloon inflation lumen 63 and the interior of the first balloon 71 and consists of a port 73 formed in the side wall forming the inner tubular member 67 adjacent the proximal extremity of the balloon 71 which opens into the balloon inflation lumen 63. Means is provided for venting the balloon 71 so that entrapped air therein can escape when the balloon is inflated and consists of self-vent of the type described in co-pending application Ser. No. 000,712, filed Jan. 6, 1987. As described, the self-vent is formed as a small bore or passage 74 in the distal extremity of the balloon 71. Alternatively, a vent tube or port leading into an inner lumen 66 can be used.

The second balloon 72 as shown is formed integral with the outer tubular member 68 and has its distal extremity secured over the proximal extremity of the first balloon 71 and is secured thereto by suitable means such as an adhesive to also provide a fluid-tight seal. As shown, the interior of the second balloon 72 is in communication with the balloon inflation lumen 64. Means is also provided for venting the balloon 72. This also can be a self-vent provided by a small passage or bore 75 in the distal extremity of the balloon. Alternatively, a vent tube can be used.

Radiopaque markers 76 and 77 of a suitable type, as for example, gold bands are mounted within the first and second balloons 71 and 72 so that the positioning of the balloons during an angioplasty procedure can be ascertained. As shown, a single marker 76 is provided between the distal and proximal extremities of the first balloon 71 and similarly, a single marker 77 has been provided between the proximal and distal extremities of the second balloon 72. It should be appreciated that if desired additional markers can be utilized in each of the balloons as, for example, placing a marker adjacent the distal and proximal extremities of the balloon rather than in the center of the balloon.

A guide wire 81 of a conventional construction is provided for use with the catheter assembly 61. It is preferably of the torquable type and is provided with a spring tip 82 which is secured to a shaft 83.

With the construction shown, to reduce diameters, the portions of the inner and outer tubular members 67 and 68 near the distal extremities have been necked down to accommodate the balloons 71 and 72 and to make it possible to provide relatively low profiles for the balloons while still retaining good flow characteristics in the distal extremities of the inner and outer tubular members 67 and 68. Thus there has been provided a catheter assembly which still provides good flow characteristics with relatively thick walls being provided to provide added stiffness for the catheter assembly. The embodiment of the catheter assembly 61 can be provided with an adapter assembly of the type similar to the adapter assembly described in connection with the catheter assembly shown in FIG. 1 which is provided with balloon inflation ports and a guide wire port.

In connection with the present invention, tandem balloon catheter assemblies have been provided in which the first balloon has diameters ranging from 1.5 to 2.5 millimeters and the second or larger balloon has diameters ranging from 2.5 to 4.0 millimeters.

The procedure for use of the tandem balloon dilatation catheter assembly of the type shown in FIG. 5 which utilizes a movable guide wire is very similar to that described in FIG. 1 with the exception that the guide wire 81 is first introduced into the guiding catheter with the spring tip being advanced into the stenosis. The catheter assembly 61 is advanced over the guide wire. The balloons 71 and 72 are used in a similar two-step procedure to open the stenosis. After the two balloons have been inflated and deflated, the catheter assembly 61 with the guide wire 81 can be removed. Thereafter, the guiding catheter can be removed.

From the foregoing it can be seen that the balloon dilatation catheter assembly of the present invention is particularly useful in opening very tight stenosis by utilizing a two-step procedure. The smaller distal balloon can be utilized to enter the tight stenosis because of its smaller profile. After a partial opening of the tight stenosis with the smaller balloon, the higher profile proximal balloon can be advanced into the stenosis and inflated to complete the dilatation of the stenosis.

By utilizing such tandem balloon dilatation catheter assemblies, it is possible to eliminate the use of a plurality of balloon dilatation catheters of increasing size in an angioplasty procedure to achieve the desired opening of the stenosis. By eliminating the use of a plurality of catheters and by providing balloon dilatation catheter assemblies having tandem balloons, it is possible to reduce the amount of time and manipulations required in performing an angioplasty procedure.

It should be appreciated that although the tandem balloon dilatation catheter assembly shown in FIG. 1 only utilizes two balloons, it is possible if desired to provide additional balloons in tandem having still larger diameters if this is found to be necessary.

What is claimed is:

1. A steerable dilation catheter for angioplasty procedures, comprising:
   (a) a first elongated tubular member;
   (b) a first dilatation balloon on the distal procedure of the first tubular member;
   (c) a second elongated tubular member having an inner lumen extending therethrough which is disposed within the first elongated tubular member and which defines therebetween an annular lumen in fluid communication with the interior of the first dilatation balloon, a distal portion of the second tubular member extending through the interior of the first dilatation balloon being sealed about the distal portion of the second tubular member extending therethrough;
   (d) a second dilatation balloon distal to the first balloon on the distal portion of the second tubular member, the inner lumen of the second tubular member being in fluid communication with the interior of the second dilatation balloon;
   (e) a guidewire or guiding member disposed within the inner lumen of the second tubular member which is fixed to prevent the removal thereof and which has a solid portion extending through the interior of the second dilatation balloon and out the distal end thereof with the distal end of the second balloon being sealed about the solid portion of the guidewire or guiding member extending therethrough;
   (f) means provided on the proximal end of the guidewire or guiding member to torque the guidewire or guiding member about the longitudinal axis thereof; and
   (g) an adapter assembly provided on the proximal ends of the first and second tubular members to facilitate the independent inflation and deflation of the first dilatation balloon through the annular lumen and the independent inflation and deflation of the second dilatation balloon through the inner lumen of the second tubular member.

* * * * *